United States Patent [19]

van der Knaap

[11] Patent Number: Plant 5,818

[45] Date of Patent: Dec. 2, 1986

[54] CHRYSANTHEMUM PLANT NAMED WESTLAND SUN

[75] Inventor: Jacques C. M. van der Knaap, DeLier, Netherlands

[73] Assignee: Ball Pan Am Plant Company, Parrish, Fla.

[21] Appl. No.: 661,054

[22] Filed: Oct. 15, 1984

Related U.S. Application Data

[63] Continuation of Ser. No. 494,561, May 13, 1983, abandoned.

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Evans

[57] ABSTRACT

A new and distinct cultivar of Chrysanthemum plant named Westland Sun characterized by its flat capitulum form; spider capitulum type, tubular yellow ray floret color which does not bronze under cooler temperatures, 70–90 mm. diameter across face of capitulum, long peduncles, uniform nine week response, and its semi-upright branching habit.

3 Drawing Figures

This is a continuation of application Ser. No. 494,561, filed May 13, 1983, now abandoned.

The present invention comprises a new and distinct cultivar of *Chrysanthemum morifolium,* Ramat., named Westland Sun.

Westland Sun is an induced mutation of Westland Pink, disclosed in U.S. Plant Pat. No. 4,589, and was selected to expand the color range of the parental cultivar.

Westland Sun was discovered and selected as a flowering plant within a flowering block of the parental cultivar by applicant in January 1977 in a controlled environment in Burg, Elsenweg, DeLier, Netherlands. Plants within the flowering block were derived from stock plants which had been irradiated as unrooted cuttings with an X-ray source of 1750 R units.

The first act of asexual reproduction of Westland Sun was accomplished when vegetative cuttings were taken by applicant from the initial selection in January 1977 in a controlled environment in Burg, Elsenweg, DeLier, Netherlands. Horticultural examination of selected units has demonstrated that the combination of characteristics as herein disclosed for Westland Sun are firmly fixed and are retained through successive generations of asexual reproduction.

Westland Sun has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Westland Sun, which in combination distinguish this Chrysanthemum as a new and distinct cultivar:

1. Flat capitulum form.
2. Spider capitulum type.
3. Lemon yellow ray floret color, which does not bronze under cooler temperatures.
4. Tubular ray florets-spider type.
5. Diameter across face of the capitulum 70–90 mm.
6. Long peduncles; length 90–200 mm.

7. Uniform nine week photoperiodic response to short days.
8. Height about 1 m. with no long days.
9. Semi-upright branching habit.

Of the many commercial cultivars known to applicant, the most similar in comparison to Westland Sun is Westland Yellow, also an irradiated mutation of Westland Pink. Westland Yellow is disclosed in applicant's U.S. Plant Pat. No. 4,889. Reference is made to attached Chart A which compares certain characteristics of Westland Sun to those same characteristics of Westland Yellow. Generally, the capitulum diameter of Westland Sun is somewhat larger than Westland Yellow, and Westland Sun does not tend to bronze under cooler temperatures.

The accompanying photographic drawings show typical inflorescence and foliage characteristics of Westland Sun, with colors being as nearly true as possible with illustrations of this type.

Sheet 1 is a color photograph in perspective view of Westland Sun.

Sheet 2 is a close-up color photograph showing more precisely the true flower color.

Sheet 3 is a black and white print of typical foliage of Westland Sun, at various stages of growth.

In the following description color references are made to The Royal Horticultural Society Colour Chart. The color values were determined between 9:00–9:30 A.M. on Dec. 1, 1982 under 2000–2500 foot candles of light intensity at Parrish, Fla.

Classification:

*Botanical.*—*Chrysanthemum morifolium,* Ramat., cv Westland Sun.

*Commercial.*—Cut spider spray.

I. INFLORESCENCE

A. Capitulum:

*Form.*—Flat.

*Type.*—Spider.

*Diameter across face.*—70–90 mm.

B. Corolla of ray florets:

*Color (general tonality from a distance of three meters).*—Yellow.

*Color.*—Top surface, 5B (immature), fading to 4C (mature), particularly at the floret tips.

C. Corolla of disc florets:

*Color (mature).*—Yellow.

*Color (immature).*—Lime-green.

D. Reproductive organs:

*Androecium.*—Present in disc florets only.

*Gynoecium.*—Present in both ray and disc florets; abundant.

II. PLANT

A. General appearance:

*Height.*—Upright, about one (1) meter.

B. Foliage:

*Color (abaxial).*—47B.

*Color (adaxial).*—47A.

*Shape.*—Deeply lobed and slightly serrated.

CHART A

| | RAY FLORET COLOR | CAPITULUM FORM AND TYPE | DIAMETER ACROSS FACE OF CAPITULUM |
|---|---|---|---|

CHART A-continued

| | | | |
|---|---|---|---|
| Westland Sun | Lemon-yellow, does not bronze under cooler temperatures | Flat, Spider | 70–90 mm. |
| Westland Yellow | Lemon-yellow, bronzes with cooler temperatures | Flat, Spider | 70–80 mm. |

| | PLANT HEIGHT | FLOWERING RESPONSE PERIOD | PEDUNCLE LENGTH |
|---|---|---|---|
| Westland Sun | 70–100 cm. | 9 weeks | 90–200 mm. |
| Westland Yellow | 70–100 cm. | 9 weeks | 90–200 mm. |

I claim:

1. A new and distinct cultivar of Chrysanthemum plant named Westland Sun, as described and illustrated, and particularly characterized by its flat capitulum form and spider capitulum type, tubular yellow ray floret color which does not bronze under cooler temperatures, 70–90 mm. diameter across face of capitulum, long peduncles, uniform nine week response, and its semi-upright branching habit.

* * * * *

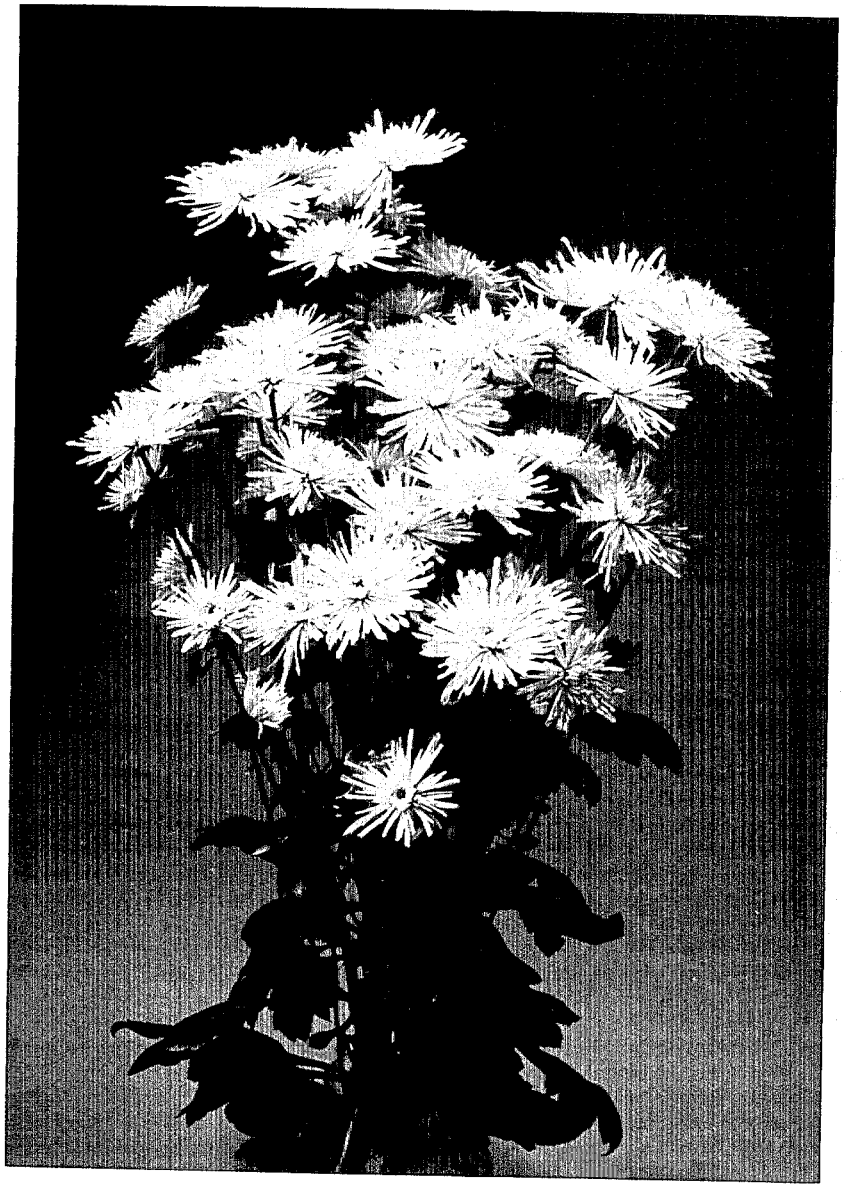

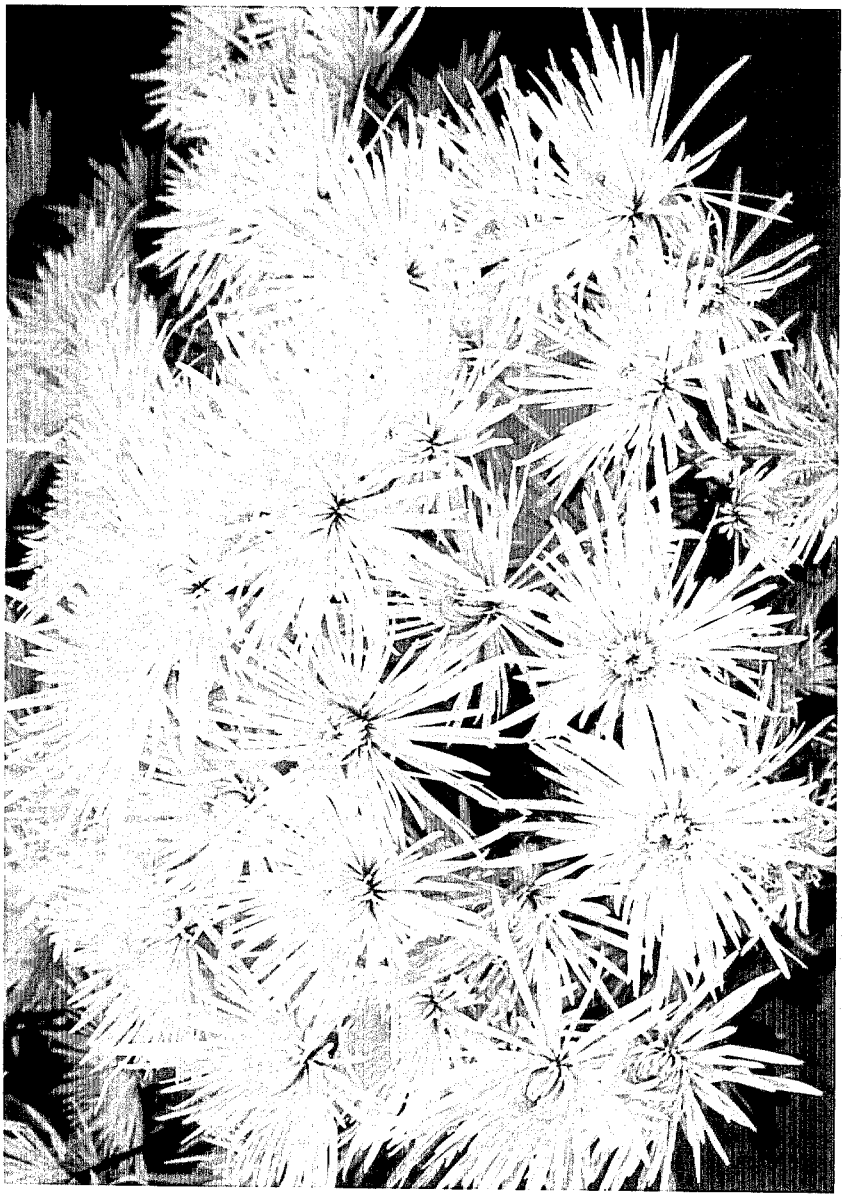

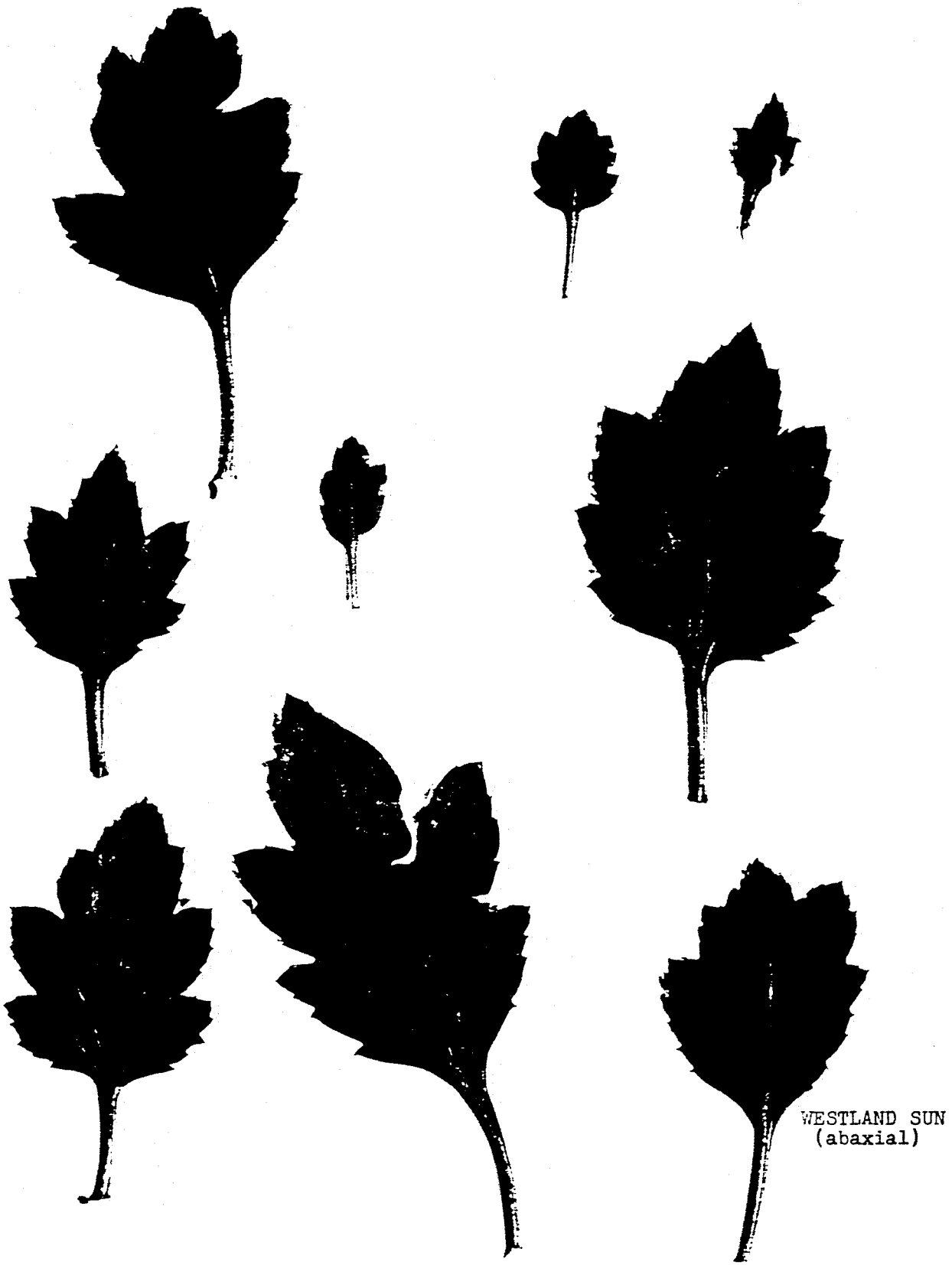
WESTLAND SUN
(abaxial)